US005608519A

United States Patent [19]
Gourley et al.

[11] Patent Number: 5,608,519
[45] Date of Patent: Mar. 4, 1997

[54] LASER APPARATUS AND METHOD FOR MICROSCOPIC AND SPECTROSCOPIC ANALYSIS AND PROCESSING OF BIOLOGICAL CELLS

[76] Inventors: Paul L. Gourley, 12508 Loyola, NE., Albuquerque, N.M. 87112; Mark F. Gourley, 7509 Spring Lake Dr., Apt. B1, Bethesda, Md. 20817

[21] Appl. No.: 407,345

[22] Filed: Mar. 20, 1995

[51] Int. Cl.$^6$ ........................................... G01J 3/30
[52] U.S. Cl. ........................ 356/318; 356/417; 250/461.2
[58] Field of Search ................................ 356/318, 301, 356/338–339, 246, 471; 372/72; 250/461.1, 461.2, 458.1, 459.1

[56] References Cited

U.S. PATENT DOCUMENTS

| | | |
|---|---|---|
| 3,916,197 | 10/1975 | Fulwyler . |
| 4,243,318 | 1/1981 | Stohr ........................................... 356/39 |
| 4,765,737 | 8/1988 | Harris ........................................ 356/336 |
| 4,947,223 | 8/1990 | Biefeld . |
| 5,100,627 | 3/1992 | Buican . |
| 5,135,304 | 8/1992 | Miles et al. ............................... 356/301 |
| 5,138,170 | 8/1992 | Noguchi ................................ 250/461.2 |
| 5,158,889 | 10/1992 | Hirako . |
| 5,245,466 | 9/1993 | Burns . |
| 5,296,963 | 3/1994 | Murahami . |
| 5,322,799 | 6/1994 | Miller . |
| 5,360,739 | 11/1994 | Fan . |

OTHER PUBLICATIONS

Leon Weiss, ed., *Histology*, 5th edition, chapter 11, pp. 447–473, (Elsevier Biomedical, 1983).

A. Ashkin, J. M. Dziedzic, and T. Yamane, "Optical Trapping and Manipulation of Single Cells Using Infrared Laser Beams," *Nature*, vol. 330, pp. 769–771, Dec. 1987.

J. K. Foskett and S. Grinstein, eds., *Noninvasive Techniques in Cell Biology*, chapter 15, pp. 375–402, (John Wiley, 1990).

Y. Kikuchi, K. Sato, H. Ohki, and T. Kaneko, "Optically Accessible Microchannels Formed in Single–Crystal Silicon Substrate for Studies of Blood Rheology," *Microvascular Research*, vol. 44, pp. 226–240, 1992.

V. V. Tuchin, "Lasers and Fiber Optics in Medicine," *Proceedings of the Society of Photoinstrumentation Engineers*, vol. 1981, pp. 2–16, 1992.

P. L. Gourley, K. E. Meissner, T. M. Brennan, and B. E. Hammons, "Surface–Emitting Semiconductor Laser Spectroscopy for Characterizing Normal and Sickled Red Blood Cells," *Proceedings of the Society of Photoinstrumentation Engineers*, vol. 2387.

*Primary Examiner*—K. Hantis
*Attorney, Agent, or Firm*—John P. Hohimer

[57] ABSTRACT

An apparatus and method for microscopic and spectroscopic analysis and processing of biological cells. The apparatus comprises a laser having an analysis region within the laser cavity for containing one or more biological cells to be analyzed. The presence of a cell within the analysis region in superposition with an activated portion of a gain medium of the laser acts to encode information about the cell upon the laser beam, the cell information being recoverable by an analysis means that preferably includes an array photodetector such as a CCD camera and a spectrometer. The apparatus and method may be used to analyze biomedical cells including blood cells and the like, and may include processing means for manipulating, sorting, or eradicating cells after analysis thereof.

43 Claims, 10 Drawing Sheets

5 nm

Emission Wavelength

LASER APPARATUS AND METHOD FOR MICROSCOPIC AND SPECTROSCOPIC ANALYSIS AND PROCESSING OF BIOLOGICAL CELLS

This invention was made with Government support under Contract No. DE-AC04-94AL85000 awarded by the U.S. Department of Energy. The Government has certain rights in the invention.

FIELD OF THE INVENTION

The present invention relates generally to invasive or noninvasive analysis and processing of biological cells, and more specifically to a laser apparatus and method for optical microscopic and spectroscopic analysis and processing of biological cells and cell components. One or more cells to be analyzed are located within an analysis region inside a laser cavity for analysis thereof in real time; and the cells may then be transported to a processing region of the apparatus for processing thereof.

BACKGROUND OF THE INVENTION

In recent years, the need for high-speed automated or semi-automated analysis and processing of biological cells and cell components has been recognized. Such analysis and processing may include a determination of morphologic characteristics of cells or differences in physical properties of cells, and is of special importance in the fields of cytochemistry, immunology, oncology, genetics, molecular biology and the like.

One method for analyzing and processing biological cells at high speed is flow and or scanning cytometry wherein the prepared cells are suspended in a carrier fluid and then are enclosed within an envelope, or sheath, stream and are passed one at a time through a sensing zone by hydrodynamic focusing. In the sensing zone, the cells are irradiated by a focused laser beam (with the cells being located outside of any laser cavity); and a light detector is used for the measurement of scattered, absorbed, or re-emitted fluorescent light. The effect that a cell has on the focused laser beam that it intercepts can be detected in a number of ways. In general, the cell has a refractive index which is different from that of the medium in which it is suspended. It will therefore scatter a portion of the laser light with which it is illuminated through a range of angles, and with varying intensities, that depend upon the refractive index difference between the cell and the surrounding carrier fluid, the cell size and shape, and any internal variations in refractive index and structure in the cell, as well as the wavelength of the illuminating light. A cell may also absorb some of the incident light, with a portion of the absorbed light being re-emitted as fluorescence, typically at an emission wavelength that is longer than the wavelength of the absorbed light. Light detectors are arranged to measure different angular intervals of the scattered or fluorescent light.

Due to a low scattering efficiency of the small size of biological cells (typically less than 15 microns in diameter) and also a limited number of sites from which fluorescence may occur, the number of photons detected for each cell moving through the focused laser beam may be small, especially compared to the number of photons in the incident focused beam. Therefore, the limits of sensitivity of the prior art flow cytometry methods for cell analysis and processing depend critically on the photon flux (i.e. power) of the incident laser beam, and the magnitude of the perturbations in the scattered or fluorescent light produced by different variants of the biological cells to be analyzed (e.g. normal versus abnormal cells).

An advantage of the present invention is that biological cells may be analyzed and processed by locating the cells within an analysis region inside a laser cavity, with the cells acting in combination with a gain medium in the cavity to generate a laser beam having information about the cells impressed (i.e. encoded) thereupon.

Another advantage of the present invention is that information related to a size, shape, and type of cell, and internal characteristics (such as DNA, RNA, nucleohistones, mitochondria, golgi bodies, endoplasmic reticulum, lysozomes, and phagosomes) thereof may be impressed (i.e. encoded) upon a laser beam in the form of an emission spectrum, a transverse mode profile, an optical intensity, a nonlinear optical signal, a lasing threshold characteristic, or a combination thereof for providing information on a status of cell activation, cell proliferation, or cell life cycle.

A further advantage of the present invention is that information selective to a portion of a cell or to a particular constituent of the cell may be impressed upon a laser beam and recovered in an analysis means, for analyzing the cell and for subsequent processing thereof.

Still another advantage of the present invention is that a biological cell may be selectively tagged with a fluorescent stain or a non-fluorescent marker (e.g. a monoclinal antibody that may act to modify the cell structure and function), with the fluorescent stain forming at least a part of the gain medium of a laser cavity containing the cell; so that upon activation of the gain medium by optical pumping, lasing may be generated at predetermined locations on or within the cell wherein the florescent stain or marker is concentrated or localized.

Yet another advantage of the present invention is that a compact biological cell analyzer may be formed according to the present invention comprising on a substrate one or more analysis regions for containing biological cells wherein laser beams may be generated at the locations of particular cells, the laser beams providing information about the cells impressed (i.e. encoded) thereupon.

Another advantage of the present invention is that a compact biological cell analyzer and processor may be formed on a substrate having at least one inlet channel for introducing the cells substantially one at a time into one or more analysis regions wherein a laser beam is generated having information about the cells impressed thereupon, and a cell processing regions proximate to each analysis region wherein different variants of the cells may be separated after analysis into a plurality of reservoirs and/or outlet channels.

A further advantage of the present invention is that a carrier fluid (e.g. a buffered saline solution) surrounding the cell may contain one or more agents such as cell stimulants, drugs, or reagents that may act to modify cell properties; and these agents may be introduced into and/or flushed from the analysis region by flow channels for analyzing a response of the cell to these agents.

These and other advantages of the apparatus of the present invention will become evident to those skilled in the art.

SUMMARY OF THE INVENTION

Accordingly, it is a primary object of the present invention to provide an apparatus for analyzing biological cells wherein at least one cell located within a resonant optical cavity of a laser acts to impress upon a laser beam generated within the cavity information about the cell, for providing a real-time analysis capability to study active metabolic cellular events.

An additional object of the present invention is to provide an apparatus for analyzing biological cells (biological cells are defined herein to include cells, cell components, cell constituents, cell fragments and the like) to determine information related to cell identity, size, shape, variants, composition, or the like by locating the cells at a fixed position in an analysis region within a laser cavity during analysis thereof, or by flowing the cells through an analysis region wherein the cells may impress (i.e. encode) such information upon a laser beam generated within the cavity and intercepting at least one cell.

A further object of the present invention is to provide an apparatus for analyzing and processing biological cells wherein a plurality of inlet channels are formed within a first or second substrate (or in one or more material layers deposited on the first or second substrate) for transport of the cells to one or more analysis regions on the substrate for analysis of the cells, and therefrom to one or more cell processing regions on the substrate, wherein the cells may be processed and distributed to a plurality of reservoirs and/or outlet flow channels.

Still another object of the present invention is to provide an apparatus that generates a laser beam in response to the presence of a biological cell in an analysis region within a laser cavity (and substantially no lasing or laser beam in the absence of a biological cell) the laser beam having one or more optical characteristics thereof determined at least in part by the presence of the biological cell or a fluorescent stain or tag associated therewith.

Yet another object of the present invention is to provide an apparatus in which one or more biological cells or components that have been prepared (i.e. tagged) with a fluorescent stain or a non-fluorescent marker (e.g. a monoclinal antibody) that is selectively localized or concentrated within one or more predetermined portions of the cells may be analyzed by locating the cells within an analysis region in a resonant optical cavity of a laser so that the florescent stain or non-fluorescent marker acts, at least in part, as a gain medium for generating optical gain and producing a laser beam having information about the cells impressed thereupon.

Another object of the present invention is to provide an apparatus for analyzing and imaging biological activity in living cells in both a native state and in a prepared state wherein the cell or cell components have been tagged with a fluorescent stain, a monoclonal antibody, an oligonucleotide, a radionuclide, or a combination thereof for observing cellular metabolic events in real time including DNA synthesis and replication, RNA synthesis and movement, protein synthesis and motion, organelle movement, nuclear programmed death (apoptosis), or the like.

An additional object of the present invention is to provide an apparatus for analyzing and imaging biological activity of cells in a native state, and a behavior of the cell in response to events including the introduction of short segments of DNA and/or RNA into the cell, and activation and proliferation at a molecular level.

Additional objects, advantages, and novel features of the invention will become apparent to those skilled in the art upon examination of the following description, or may be learned by practice of the invention. The objects and advantages of the invention may be realized and attained by means of the instrumentalities and combinations particularly pointed out in the appended claims.

To achieve the foregoing and other objects, and in accordance with the purposes of the present invention as described herein, a laser apparatus for microscopic and spectroscopic analysis and processing of biological cells is provided. The apparatus includes a laser comprising a resonant optical cavity formed by at least two reflecting mirrors, a gain medium within the resonant optical cavity, and pump means for activating the gain medium; and an analysis region within the resonant optical cavity for containing one or more biological cells to be analyzed. A laser beam may be generated by the laser in response to each biological cell present within a central portion of the cavity containing the analysis region, the laser beam having information about the biological cell impressed (i.e. encoded) thereupon. The apparatus according to the present invention may further comprise analysis means for receiving or detecting the laser beam and recovering the information about the biological cells and for generating one or more outputs thereof for display or for activating processing means for processing of the cells. (Processing of cells is defined herein to include sorting of cells according to variants thereof, or removing abnormal cells by laser eradication thereof, or other manipulations of cells according to identity, size, shape, variants, composition, or the like as known to the art.) Additionally, the apparatus may include a flow cell for transporting the biological cells substantially one cell at a time through the analysis region within the resonant optical cavity of a laser, or a plurality of flow cells for simultaneously analyzing and processing many cells.

Other objects, advantages and novel features of the invention will become apparent from the following detailed description thereof when considered in conjunction with the accompanying drawings.

BRIEF DESCRIPTION OF THE DRAWINGS

The accompanying drawings, which are incorporated into and form a part of the specification, illustrate several aspects of the present invention and, together with the description, serve to explain the principles of the invention. The drawings are only for the purpose of illustrating preferred embodiments of the invention and are not to be construed as limiting the invention. In the drawings.

DETAILED DESCRIPTION OF THE INVENTION

Figure 1:
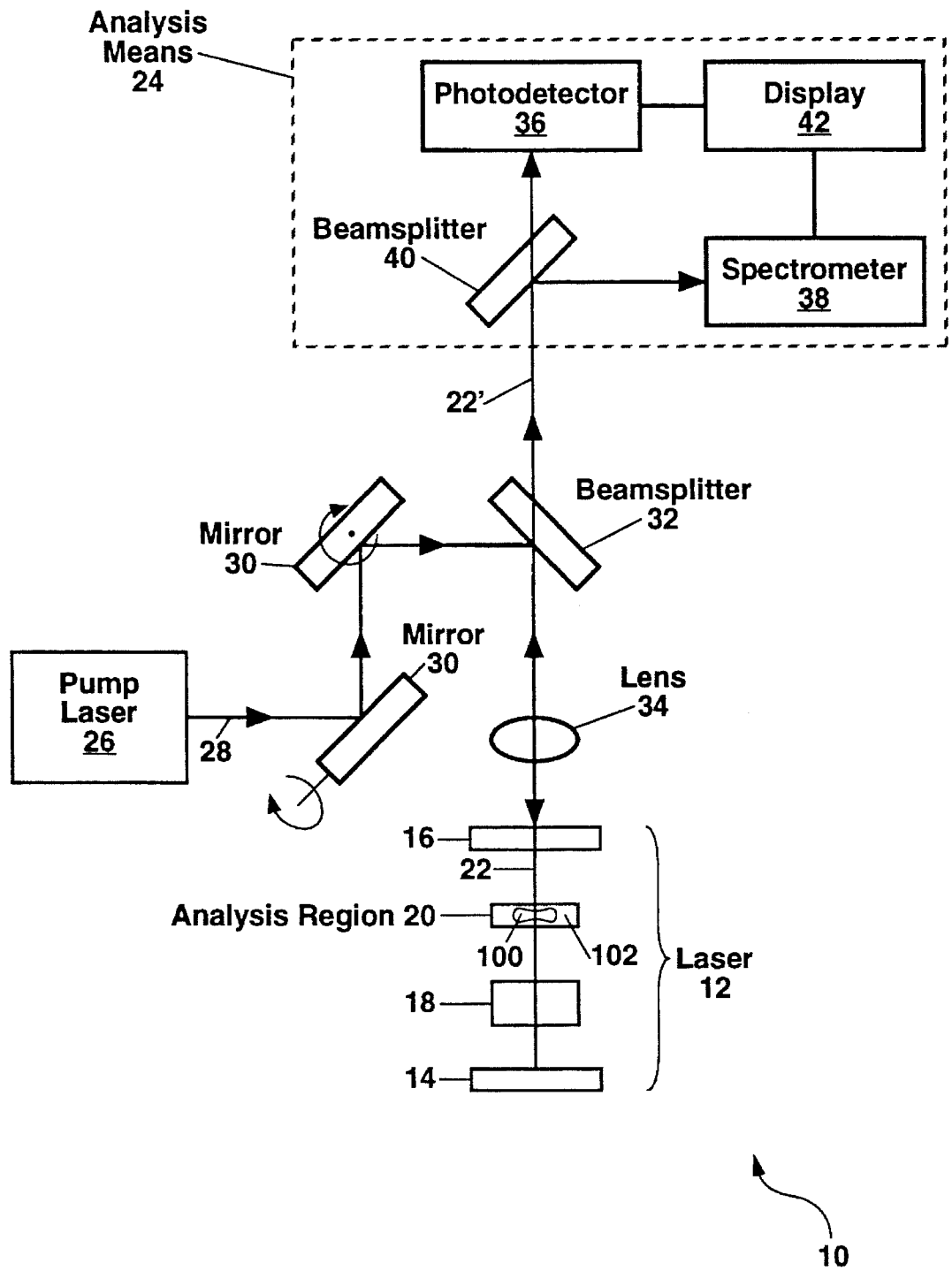
FIG. 1 shows a schematic diagram of a laser apparatus for microscopic and spectroscopic analysis and processing of biological cells according to the present invention.

Referring to FIG. 1, there is shown a schematic diagram of a laser apparatus for microscopic and spectroscopic analysis and processing of biological cells according to the present invention. The apparatus 10 comprises a laser 12 having a resonant optical cavity formed by at least two reflecting mirrors (e.g. a lower mirror 14 and an upper mirror 16), a gain medium 18 within the cavity, and an analysis region 20 within the resonant optical cavity for locating at least one biological cell 100 to be analyzed. (The present invention in which cells are located within a resonant optical cavity of a laser is to be distinguished from prior art cell analysis methods that locate the cells outside any laser cavity.) Pump means are provided for activating the gain medium for generating optical gain within the cavity. A laser beam 22 is generated by the laser in response to each biological cell present within a central portion of the cavity, with the laser beam having impressed thereupon information about the biological cell 100. The apparatus may further comprise analysis means 24 for receiving a portion 22' of the laser beam 22 from the laser 12 and recovering the information about the biological cell.

The laser 12 preferably operates at a wavelength that is at least partially transmitted through each cell 100 to be analyzed. In general, a laser 12 operating at a wavelength of about 600 to 1500 nanometers is to be preferred since many biological cells and carrier fluids 102 for transporting cells are transparent at least in part over this wavelength range. The types of lasers 12 that may be used for practice of the present invention include gas, organic dye, solid state, and semiconductor lasers. An especially well-suited type of laser 12 for practice of the present invention is a vertical-cavity surface-emitting semiconductor laser as shown in FIG. 3.

The laser 12 includes a pump means for activating the gain medium 18. The pump means may be an optical pump means comprising a pump laser 26 (as shown in FIG. 1) or a lamp as may be preferred for activating a gain medium 18 in an organic dye, solid state, or optically-pumped semiconductor laser 12. Alternately, the pump means may be an electrical current flowing through a semiconductor p-n junction as in an electrically-injected semiconductor laser 12 such as a vertical-cavity surface-emitting laser; or an electrical current flowing across a discharge as in a gas laser 12. The pump means may be operated either continuously or in a pulsed mode to generate either a continuous-wave (cw) or pulsed lasing beam 22. A pulsed pump means including a nanosecond, picosecond, or femtosecond pump laser 26 may be preferred for an optically-pumped laser 12 to provide a high electron-hole density in the gain medium 18 thereby increasing the gain therein. (As the gain in the gain medium is increased, the gain bandwidth of the gain medium increases, resulting in a wider spectral width of the laser beam 22 and lasing in a larger number of longitudinal and transverse cavity modes.)

In the case of an optical pump means for activating the gain medium 18 as shown in FIG. 1, a pump laser 26 may generate a pump beam 28 that may be directed through a partially transmitting or dichroic upper mirror 16 into the gain medium 18, for example, by a pair of beam directing mirrors 30, a beamsplitter 32 (or otherwise a dichroic mirror that substantially reflects the pump beam 28 while substantially transmitting the portion 22' of the laser beam 22 to the analysis means 24), and a lens 34. The pump beam 28 is preferably focused into a small spot of about 100 microns or less within the gain medium. Each beam directing mirror 30 preferably includes steering means such as a galvanometer, an acousto-optic beam deflector, an electro-optic beam deflector, or the like for steering the pump beam 28 to activate a particular portion of the gain medium 18. The optical pump means may be directed through a microscope, with the beamsplitter 32 and the lens 34 being part of an optical train within the microscope.

For practice of the present invention for analyzing biological cells, the pump beam is preferably directed into the gain medium 18 so that the activated portion of the gain medium lies along a central portion of the resonant optical cavity of the laser 12 in line with the analysis region 20 so that each biological cell 100 may act as a lens, optical waveguide, or dispersive optical element to redirect light rays within the cavity leading to the generation of a laser beam 22 in combination with the gain medium 18.

The analysis region 20 is located within the cavity of the laser 12 as shown in FIG. 1. The analysis region may be in the form of a container for holding one or more biological cells 100 in a fixed position; or the analysis region may be a channel region of a flow cell for transporting cells at a high-speed through the analysis region 20. For an analysis region 20 in the form of a container, the lateral dimensions of the analysis region may be many times larger than the size of the cells to be analyzed so that a plurality of cells 100 may be placed in the analysis region (with the cells preferably in a carrier fluid 102) and individually analyzed, for example, by steering the pump beam 28 to the location of a particular cell and thereby activating the portion of the gain medium 18 in superposition with the cell (e.g. below the cell). After the analysis of a particular cell 100, the pump beam may be steered to different locations within the analysis region 20 for the analysis of other cells.

The analysis region 20 may also be a channel region of a flow cell. In this case, the channel region may have transverse dimensions perpendicular to a flow direction that are constricted to dimensions down to about twice the size or less of the cells to be analyzed so that the cells 100 may be transported in a carrier fluid 102 substantially one cell at a time through the central portion of the resonant optical cavity for analysis thereof. The channel region may be further constricted in one or more transverse dimensions for orienting the cells 100 in a particular direction. For example, when processing red blood cells (i.e. erythrocytes) that have a biconcave shape, it may be preferable to limit the channel height (i.e. the transverse dimension of the analysis region oriented parallel to the laser beam 22 in FIG. 1) to about 5 microns or less to orient the cell as shown in FIGS. 1–3. In general, the transverse dimensions of the channel region will be predetermined depending upon the types or variants of cells to be analyzed and processed by the apparatus 10.

When the analysis region 20 is a channel region of a flow cell, means for supplying the biological cells to the analysis region may be connected to one side of the flow cell (i.e. to an inlet channel), and means for accumulating the biological cells may be connected to the other side of the flow cell (i.e. to an outlet channel). The means for supplying the biological cells to the analysis region may be positive displacement pumps, or syringes, or the like as known to the art; and such supply means may result in the transport of the cells 100 through the analysis region 20 at a variable or a controlled high speed. The means for accumulating the biological cells may include one or more cell processing regions, or means for processing a plurality of cells wherein the cells are selectively tagged or sorted in response to information gathered by the apparatus 10 (e.g. inresponse to signals received from the analysis means 24).

The cell processing means may provide for sorting of cells according to variants thereof, or for removing abnormal cells by laser eradication thereof, or for other manipulations of cells according to identity, size, shape, variants, composition, or the like as known to the art. The cell processing means may include, for example, a nozzle mounted upon a piezoelectric transducer for converting a flow stream in a flow cell of the apparatus 10 into a plurality of constant volume droplets, each droplet containing a cell to be processed. The cell processing means may act to electrically charge the individual droplets in response to a signal received from the cell analysis means 24, with the cells then being directed through a static electric field whereby droplets with different charges are deflected into different reservoirs or flow channels of the cell processing means. Such processing of cells by means of an electric field is commonly used in the art of flow cytometry (but with the cells being located outside of any laser cavity), and is disclosed, for example, in U.S. Pat. No. 4,765,737 to Harris et al, which is incorporated by reference herein.

The cell processing means may further include one or more manipulation lasers for manipulating, sorting, or eradicating the cells during processing thereof. The use of laser beams for the manipulation or sorting of cells (e.g. so called "optical tweezers") is disclosed in an article by A. Ashkin, J. M. Dziedzic, and T. Yamane entitled *"Optical Trapping and Manipulation of Single Cells Using Infrared Laser Beams,"* published in Nature, volume 330, pages 769–771, December 1987; and in a book entitled "Noninvasive Techniques in Cell Biology," edited by J. K. Foskett and S. Grinstein, chapter 15, pages 375–402, published by John Wiley, 1990, both of which are incorporated by reference herein.

Cell manipulation, sorting, or the like may be performed by the use of a focused laser beam (preferably at an infrared wavelength) that acts to trap or entrain a cell within the focused laser beam and thereby allow the cell to be moved by optical radiation pressure (i.e. photon momentum) at velocities of up to about 500 $\mu m$-$s^{-1}$ or more as the laser beam is steered. In this manner a plurality of biological cells 100 in a carrier fluid 102 may be manipulated or sorted after analysis according to identity, size, shape, variants, composition, or the like, and transferred to different reservoirs or flow channels as shown in a third example of the present invention in FIG. 4.

Another form of cell processing that may be practiced according to the present invention is cell eradication in which a laser beam is used at a power level of about 50–100 milliWatts or more to destroy a biological cell 100 after analysis. For laser eradication of cells, it may be preferable to use a laser operating at ultraviolet or visible wavelengths since cells have a higher absorption at these wavelengths as compared to infrared wavelengths. Furthermore, the laser manipulation of cells by optical trapping may be substantially modified or enhanced by the presence or absence of a multi-beam interference effect within the cavity of the laser 12 (i.e. the use of "laser tweezers" may be practiced according to the present invention within the cavity of a laser as compared with the prior art usage of "laser tweezers" outside of any laser cavity).

In FIG. 1, the portion 22' of the laser beam 22 generated in the laser 12 (due to the presence of a cell within the central portion of the cavity) is directed into the analysis means 24 for microscopic and/or spectroscopic analysis of the cell. The analysis means 24 may be beam-coupled or fiber-coupled to the beam 22', and preferably includes a photodetector 36 and a spectrometer 38 for microscopic and spectroscopic analysis, respectively wherein the information about the biological cells 100 is recovered. The analysis means 24 may further include a beamsplitter 40 or the like for dividing the beam 22' into two or more analysis beams. The analysis means 24 also preferably includes a display 42 which may include a computer or the like for receiving outputs from the photodetector and spectrometer and digitizing, recording, and displaying the information recovered from the cells; and/or comparing the recovered information with a look-up table for identifying identity, size, shape, variants, composition, or the like; and for providing one or more output signals to the cell processing means for subsequent processing of the cells.

In some embodiments of the present invention, the analysis means 24 may be part of an existing microscopic analysis system (e.g. a microscope), with the analysis means 24 being as simple as an imaging camera 36 (sensitive to infrared light) and a television monitor 42. In this case, the apparatus 10 may be used, for example, for a manual microscopic analysis of biological cells, with images of the cells viewed in real time at a video rate.

In other embodiments of the present invention, the analysis means 24 may be compactly formed (e.g. as an array photodetector 36 and/or a spectrometer 38 integrated on a semiconductor chip) so that the analysis means may be located near or incorporated with the laser 12 and the analysis region 20, thereby forming a compact or integrated apparatus 10 for cell analysis and processing.

Microscopic analysis may be performed with the photodetector 36 which may be a single-element detector such as a photodiode or photomultiplier tube or the like for measuring an optical intensity of the portion 22' of the laser beam 22 incident upon the photodetector. Alternately, the photodetector may be a one- or two-dimensional detector array of photodiodes or a charge-coupled detector (CCD) forming an imaging camera for measuring a transverse mode profile of the incident portion of the laser beam 22. Such an imaging camera may enable a video display to be formed for the operator to direct the operation of the apparatus 10 and to observe the progress in processing and analyzing the biological cells 100. The video display may include white- or infrared-light reflectance or transmittance images of cells as well as images of the incident portion 22' of the laser beam.

A spectroscopic analysis of the portion 22' of the laser beam 22 may be performed with the spectrometer 38 which may include a diffraction grating, prism, or the like for dispersing the portion 22' into its component wavelengths, and a one-dimensional array photodetector for detecting those components to generate a spectrum thereof. The spectrometer 38 may be a stand-alone instrument used with the apparatus 10; or the spectrometer may be integrated into the apparatus in a hybrid or integrated fashion (e.g. as an optical integrated circuit). The spectrometer 38 may also operate in real time at a video rate for display and/or analysis of the spectrum.

Figure 2A:
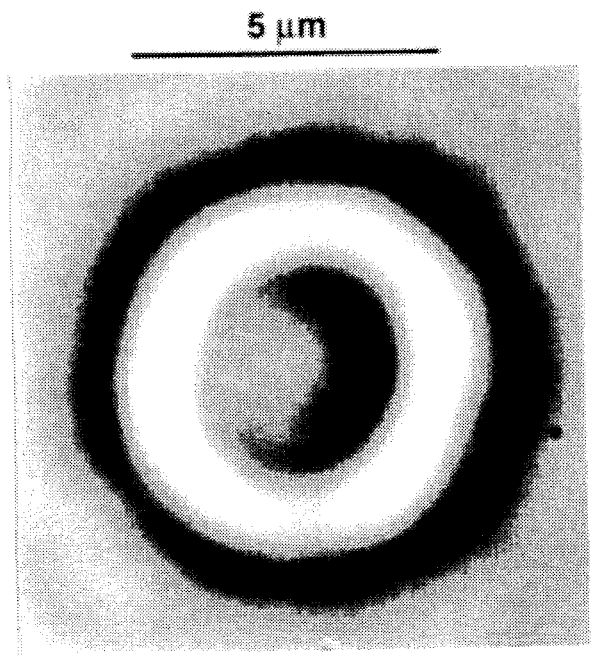
FIG. 2a shows a transmitted light image of a normal human red blood cell illustrating that different portions of a cell may redirect light differently.
Figure 2B:
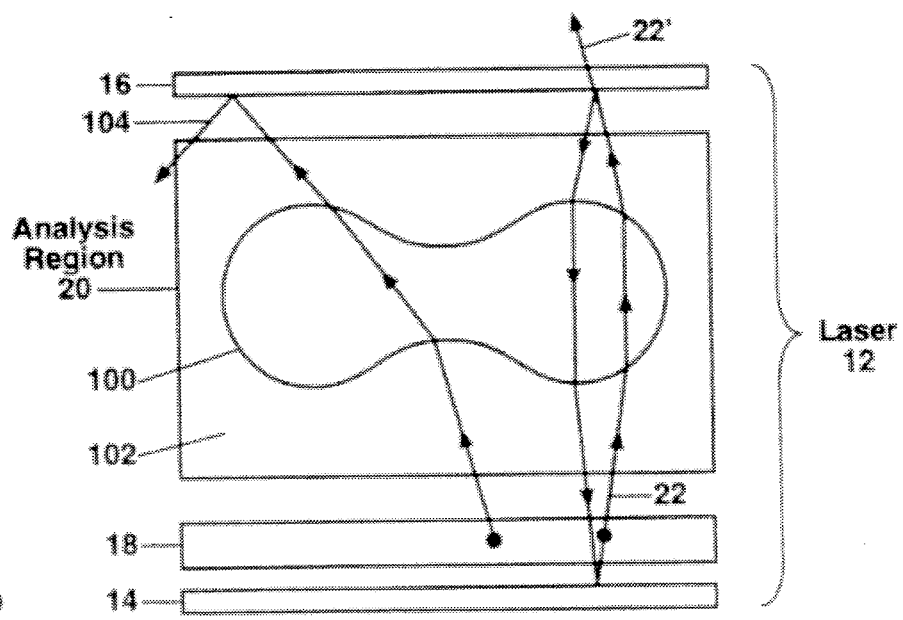
FIG. 2b shows a schematic illustration of a red blood cell in the apparatus of the present invention to illustrate how the cell may act to redirect light rays in the apparatus and determine the location and shape of a laser beam generated in the apparatus.

The present invention may be understood with the example of FIG. 2. FIG. 2a shows a photograph of a normal human red blood cell recorded in transmission with an infrared light source. Normal red blood cells 100 have the shape of biconcave disks with a diameter of about 7 μm and a thickness of about 2 μm. The red blood cell in FIG. 2a has a relatively smooth outer surface defined by a cytoskeletal network of spectrin with a very small surface roughness (less than 50 nm) so that optical scattering is low. The surface includes a convex region near the cell circumference and a concave central region as shown in a side view of the cell in FIG. 2b. The interior of the red blood cell is relatively transparent at an infrared wavelength of, for example, about 850 nm so that the cell may be viewed as a lens with a focal length that varies across the cell diameter (or alternatively as an optical waveguide). The structure of blood cells is described in a book entitled "Histology", chapter 11, pages 447–473 published by Elsevier Biomedical, 1983 which is incorporated by reference herein.

In FIG. 2a, the bright annulus in the transmitted light image corresponds to the convex region of the red blood cell (with a side view substantially as shown in FIG. 2b). In this region, the cell acts as a lens to redirect or focus the transmitted infrared light in a direction substantially normal to the top surface of the cell, allowing the light to be imaged in the photograph of FIG. 2a. However, in the concave central region of the cell in FIG. 2a, the transmitted infrared light is redirected off-axis so that this portion of the transmitted light image appears dark.

This lens-like nature of cells is typical of many types of normal or abnormal cells (including red and white blood cells, platelets, muscle cells, neural cells, sperm cells, and the like) with or without a nucleus; and this lens-like nature is due to the relatively high transmission of cells at infrared wavelengths and to the difference in the refractive index of the cells compared to the surrounding carrier fluid 102. The refractive index of a red blood cell 100 is determined primarily by a complex formed by the internal hemoglobin and outer spectrin layer. The complex has a refractive index that is about 2% higher than a carrier fluid 102 such as a blood plasma that may surround the cell. The refractive indices of the internal hemoglobin and the outer spectrin are nearly identical. At an infrared wavelength of about 850 nm, the absorption coefficients of hemoglobin and water are both less than $10^{-2}$ cm$^{-1}$. Thus, red blood cells at infrared wavelengths may be considered to be nearly perfect optical elements (i.e. lenses) with little optical scatter or loss. Due to this high optical quality, the cells may be used as intracavity optical elements within the laser 12 to aid in generating a laser beam 22.

Other types of biological cells show similar infrared light transmission effects, although the contrast may be reduced compared to the red blood cell of FIG. 2a. For example, a white blood cell (i.e. a leukocyte) may show three bright inner regions corresponding to segments of the nucleus within the white blood cell. The same optical focusing effects, though at lower contrast, are present in cells in their hydrated physiologic state.

This is further illustrated in FIG. 2b which shows a schematic side view of the laser 12 with a red blood cell 100 surrounded by a carrier fluid 102 such as a blood plasma in the analysis region 20 within the laser. For red blood cells, the refractive index of hemoglobin is about 1.40 compared to about 1.35 for blood plasma. Thus, the entire red blood cell may act as a lens inside the cavity of the laser 12. In the case of a white blood cell, a DNA/protein complex in the nucleus of the cell has a higher refractive index than the surrounding cytoplasm, thereby acting as a lens. Furthermore, the white blood cell as a whole has a higher refractive index than the surrounding carrier fluid and may act as a lens also. Thus the white blood cell may have two lens-like entities (i.e. the entire cell and the nucleus within the cell); with each lens-like entity acting in the apparatus 10 to produce a distinct set of transverse lasing modes (as shown in FIG. 10) which can be used to analyze and process a plurality of white blood cells. Other lens-like entities in a white blood cell may be formed by components of the cell including the nucleolus, golgi bodies, and endoplasmic reticulum.

The net result in FIG. 2b is that infrared light passing through any biological cell may be concentrated or channeled into the higher-refractive-index regions of the cell. This may be observed with only a single pass of infrared light through the cell as in the transmitted light image of FIG. 2a.

In FIG. 2b, the gain medium 18 upon activation by the pump means generates a plurality of photons which are emitted out from the gain region. Some of these photons may be redirected through a portion of the cell along a substantially closed path between the reflecting mirrors (14 and 16) to resonate within the cavity, stimulating the emission of additional photons and leading to lasing action and the generation of a laser beam 22 with a stable optical mode within this portion of the cell. Other photons may be redirected through other portions of the cell in an off-axis direction (e.g. along the path 104 in FIG. 2b) so that no closed path between the reflecting mirrors occurs, with the result that no laser beam is generated in these other portions of the cell.

Figure 5:
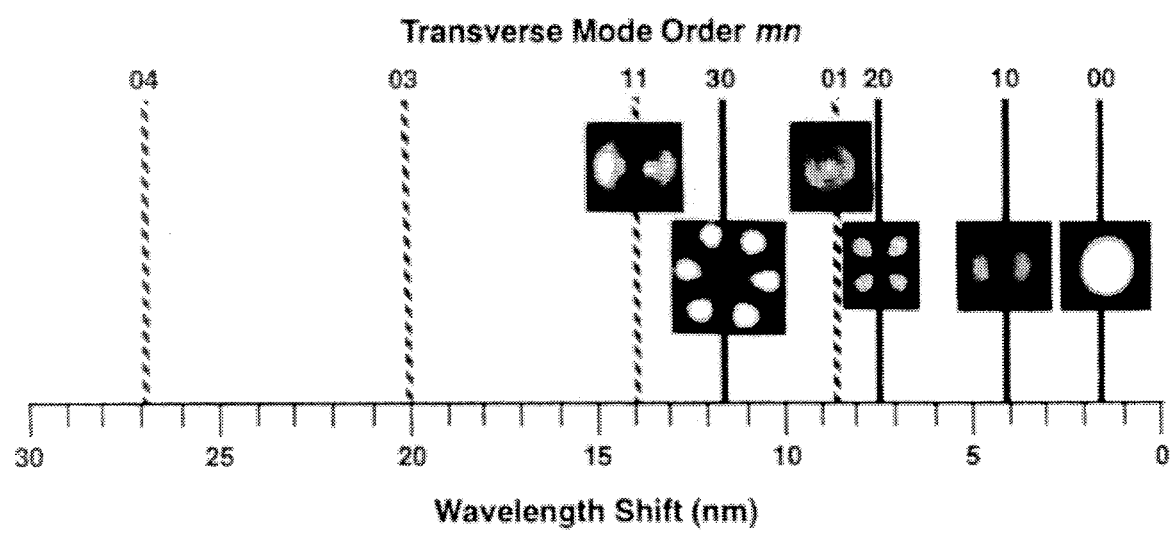
FIG. 5 shows calculated wavelength shifts of a cell in the apparatus measured relative to the unperturbed laser cavity, with the inset photographs showing profiles for the various transverse modes that may be excited to lase in the apparatus by the presence of a normal human red blood cell.

Thus, portions of biological cells may act as lenses or optical waveguides to increase an optical confinement of light generated within the gain medium 18 in a laser 12. By placing the cells inside the laser cavity, the effect of even small differences in refractive index or shape in the cells may be amplified, resulting in the generation of a laser beam 22 having one or more stable transverse modes defined at least in part by the cells. Such stable transverse modes may be theoretically calculated by a ray tracing analysis which allows a wavelength shift (relative to a fundamental lasing mode of the laser cavity in the absence of any cell or carrier fluid) for each stable mode to be determined and plotted as shown in FIG. 5. This transverse mode analysis is described in detail in a paper by P. L. Gourley, K. E. Meissner, T. M. Brennan, and B. E. Hammons entitled "*Surface-Emitting*

*Semiconductor Laser Spectroscopy for Characterizing Normal and Sickled Red Blood Cells*," presented at the International Symposium on Biomedical Optics in San Jose, Calif., Feb. 4–10, 1995; and to be published in the Proceedings of the Photonics West '95 Conference, volume 2387, by the Society for Photoinstrumentation Engineers.

From the illustration of FIG. 2b, it may be seen that the laser beam 22 may have information impressed thereupon about the biological cell 100 by placing the cell within an analysis region 20 inside the cavity of a laser 12. This cell information may be recovered by measuring an emission spectrum, a transverse mode profile, an optical intensity, or combinations thereof of a portion 22' of the laser beam 22 with the analysis means 24 of FIG. 1. By generating a laser beam 22 in the apparatus 10 of the present invention, a much larger analysis light signal (i.e. a larger photon flux) may be generated than may be possible for prior art analysis methods as described heretofore in which the cells are located outside any laser cavity, with the analysis signal being in the form of scattered or re-emitted fluorescent light.

In the example of FIG. 2b, the biological cell 100 (including cell components) may also be tagged prior to being placed into the analysis region 20 or transported thereto. By preselecting a fluorescence stain that may be excited by a pump laser 26 to emit at an infrared wavelength matched to the gain medium 18, the fluorescence emission generated within the cell may be additive to the gain produced within the gain medium 18, thereby lowering a threshold for lasing in the cavity and aiding in impressing (i.e. encoding) information about the cells 100 upon the laser beam 22 generated within the laser 12. In this manner, a selective staining of a biological cell (including cell components) may be used to generate a laser beam 22 passing through the stained portions of the cell, thereby allowing the analysis of constituent matter within the cell, or aiding in the identification of cell variants. In some embodiments of the present invention, it may be possible to locate the gain medium as a fluorescent marker entirely within cells to be analyzed, thereby simplifying the construction of the laser 12 (for example, to simply a pair of reflecting mirrors surrounding an analysis region) and eliminating the need for a gain medium 18 separate from the cells to be analyzed.

Figure 3A:
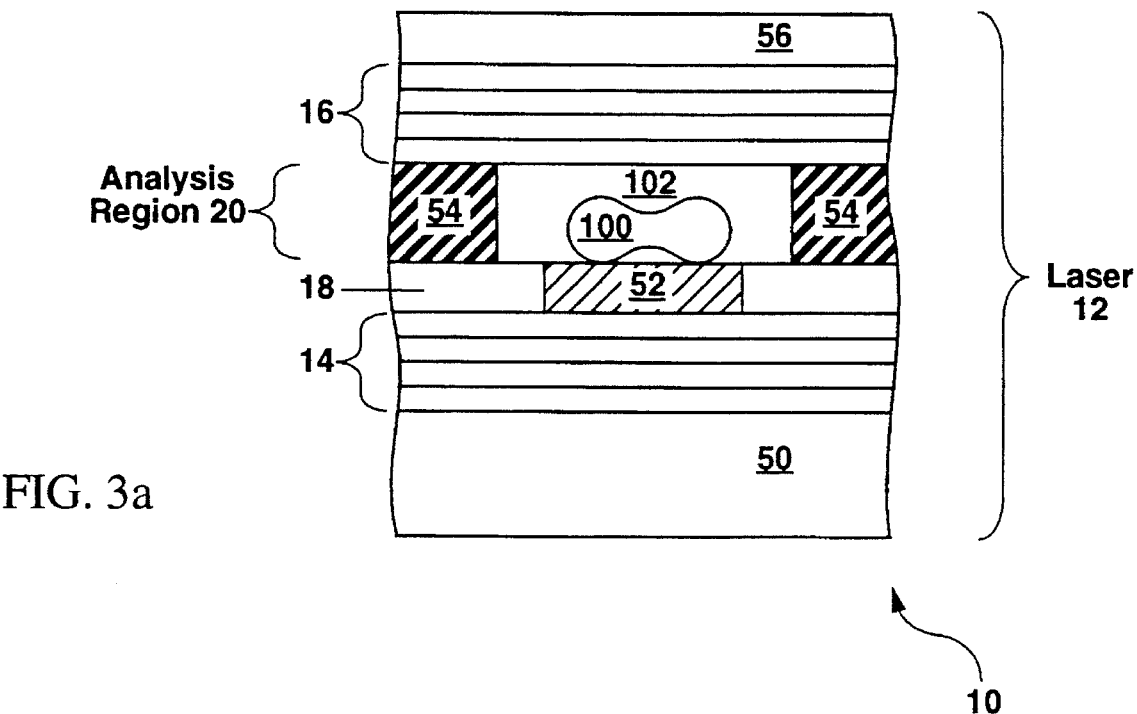
FIGS. 3a and 3b show first and second examples, respectively, of a vertical-cavity surface-emitting semiconductor laser biological cell analyzer according to the present invention.

FIG. 3a shows a first example of an apparatus 10 for analyzing biological cells according to the present invention. In FIG. 3a, the laser 12 is an optically-pumped vertical-cavity surface-emitting semiconductor laser. The laser 12 comprises on a semiconductor substrate 50 a lower reflecting mirror 14, a semiconductor gain medium 18, a patterned analysis region 20, and an upper reflecting mirror 16.

The use of a semiconductor laser such as a vertical-cavity surface-emitting laser 12 in FIG. 3 may be preferred for practice of the present invention due to the high gain available in a semiconductor gain medium 18 which may provide compensation for an absorption or scattering loss in the cells to be analyzed.

The semiconductor substrate 50 may be, for example, a III-V compound semiconductor such as gallium arsenide (GaAs), indium phosphide (InP), or the like as disclosed in U.S. Pat. No. 4,947,223 and references therein which are incorporated herein by reference; or the substrate 50 may be a micromachineable material such as silicon with a lower reflecting mirror 14 and a gain medium 18 formed thereupon or attached thereto. The lower reflecting mirror 14 preferably comprises a distributed Bragg reflector mirror formed from a plurality of alternating one-quarter wavelength thick layers of high- and low-refractive-index semiconductor materials such as GaAs and aluminum-gallium-arsenide (AlGaAs), respectively. The lower reflecting mirror 14 may be formed on the semiconductor substrate or wafer by epitaxial growth methods such as molecular beam epitaxy (MBE), metal-organic chemical vapor deposition (MOCVD), or the like. The lower reflecting mirror may have a reflectivity at a lasing wavelength in the infrared of about 95 to 99% or more. As an example, a lower reflecting mirror 14 may be formed from 28.5 periods of alternating layers of low-index AlAs (about 620 nm thick) and high-index $Al_{02}Ga_{0.8}As$ (about 7 15 nm thick) for use at a lasing wavelength near 850 nm.

The semiconductor gain medium 18 may be grown above the lower reflecting mirror 14 by the same epitaxial growth method used for forming the lower mirror. The semiconductor gain medium 18 may comprise a bulk semiconductor such as GaAs or indium-gallium-arsenide (InGaAs) with a thickness of about 50 to 150 nanometers; or the gain medium 18 may include one or more quantum-well layers separated by barrier layers having an energy bandgap higher than the energy bandgap of the quantum-well layers to form a single- or multiple-quantum-well gain medium. In the latter case, the quantum-well layers may have thicknesses of about 5 to 30 nanometers; and the barrier layers may have a thickness up to about 250 nm. Unstrained or strained quantum-well layers and barrier layers may be used for forming the vertical-cavity surface-emitting semiconductor laser 12 in FIGS. 3a and 3b. Furthermore, one or more quantum-well layers may be located at predetermined positions within the gain medium 18 to provide a periodic gain therein, or to position an electric field node or antinode within a particular part of the cavity (e.g. at the location of a particular component within one or more cells to be analyzed).

In FIG. 3a, an activated portion 52 of the gain medium 18 may be generated in response to a laser pump beam 28 propagating downwards through the upper reflecting mirror 16 into the gain medium. (The upper reflecting mirror 16 is preferably a dichroic mirror with a high transmission at a pump wavelength of the laser pump beam 28 and a high reflectivity at a lasing wavelength of the laser 12.) The activated portion 52 may circular or otherwise shaped (when viewed from above) with a size of about 20 to 100 microns, with the activated portion preferably being located in superposition with (e.g. below) a biological cell 100 to be analyzed. The location of the activated portion 52 may be moved (e.g. within a large-area gain medium 18 having lateral dimensions of about 0.1 to 10 cm) by steering the pump laser beam 28 to a different location within the gain medium 18 for analyzing a plurality of cells in an analysis region 20 superposed with the gain medium.

Figure 3B:
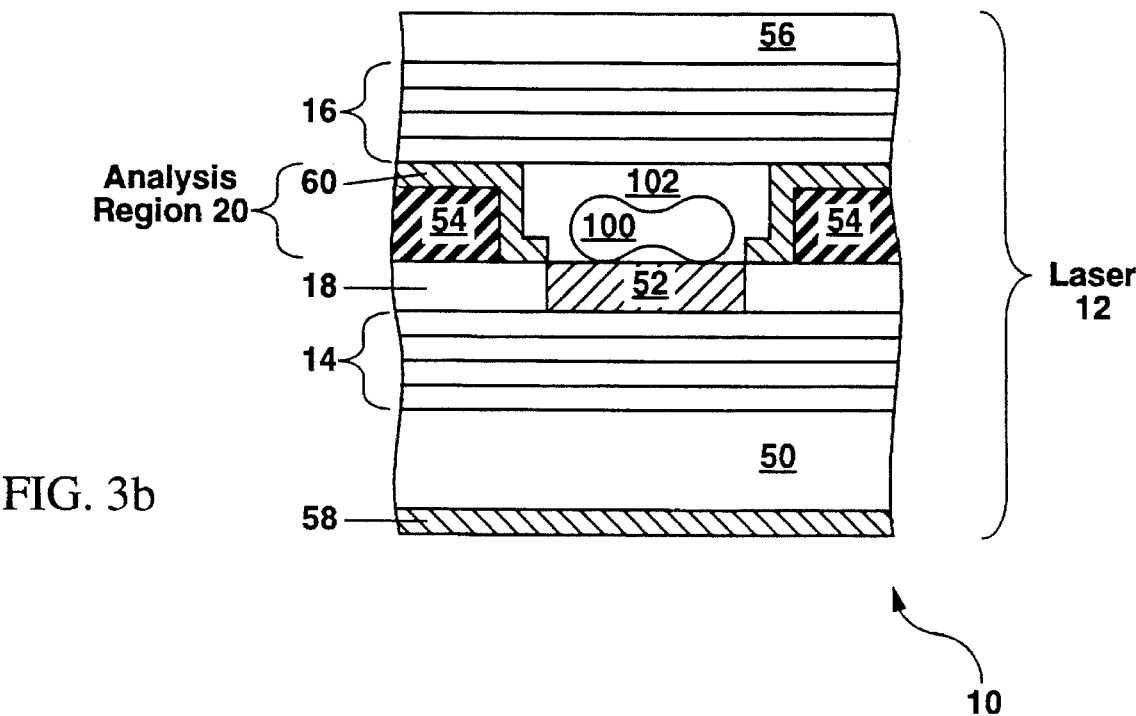

The biological cell 100 is preferably surrounded by a carrier fluid 102 (e.g. a buffered saline solution) within the analysis region 20 as shown in FIGS. 3a and 3b. The analysis region 20 in FIG. 3a is preferably formed above the gain medium 18 by etching down through semiconductor layers formed on the substrate 50, or by a deposition and patterning process, and thereby forming a container or flow channel for one or more cells. (Alternately, the analysis region may be formed on the mirror side of the transparent substrate 56, for example, prior to depositing the upper reflecting mirror 16.) The process for forming the analysis region may also form additional elements of the apparatus 10, including one or more flow channels, reservoirs, and cell processing regions.

The analysis region 20 may comprise, for example, a patterned insulating layer 54 formed by depositing or spinning on an insulating material preferably including a biocompatible capping layer therein by Mar. 20, 1995 such as silicon nitride, or silicon dioxide, or a photoresist, polyimide, glass, epoxy resin, or the like above the gain medium 18, and patterning the insulating layer to form one or more containers or flow channels therein. (The patterning of the insulating layer may be performed by an etching or lift-off process as known to the semiconductor processing art.)

In FIG. 3a, the upper reflecting mirror 16 is located above the analysis region 20, preferably forming a liquid-tight seal therewith. The upper reflecting mirror 16 may be a dielectric mirror formed, for example, from a plurality of alternating one-quarter wavelength layers of high- and low-refractive index dielectric materials deposited on a transparent (i.e. substantially transparent to infrared light) substrate 56 such as glass, fused silica, sapphire, or the like. (Alternately, the upper reflecting mirror 16 may be formed on a transparent semiconductor substrate 56 in a manner similar to the formation of the lower reflecting mirror 14.) The upper reflecting mirror 16 may be permanently attached to the analysis region 20 by means of an adhesive or the like to form, for example, a flow cell for transporting cells substantially one at a time through the analysis region; or the upper mirror may be detachable from the analysis region 20 for forming, for example, a static cell or container wherein one or more cells may be manually placed for analysis. In the case of a detachable upper mirror 16, the upper mirror may be held in place by gravity or by a clamp or the like, with or without forming a liquid-tight seal between the upper mirror and the analysis region.

In some embodiments of the present invention, the lower reflecting mirror 14 and the gain medium 18 may be formed on a semiconductor growth substrate and subsequently removed therefrom (e.g. by polishing and/or etching away the growth substrate, or by selectively etching under the lower mirror and lifting off the lower mirror and gain medium) for attachment to a micromachined substrate 50 (e.g. a silicon substrate) for formation of the laser 12. This method is particularly applicable for the formation of an optically pumped laser 12, and may be preferred for some embodiments of the present invention such as the compact biological cell analyzer and processor in the example of FIG. 4.

FIG. 3b shows a second example of an apparatus 10 for analyzing biological cells according to the present invention. In FIG. 3b, the laser 12 is an electrically-injected vertical-cavity surface-emitting semiconductor laser. Such a laser may be formed, at least in part, in a manner similar to that described with reference to FIG. 3a. For an electrical excitation of the gain medium in FIG. 3b (i.e. an electrical pump means), a p-n junction is formed within or surrounding the semiconductor gain medium 18; and the lower reflecting mirror 14 and the substrate 50 are both doped either n-type or p-type (to about $10^{18}$ cm$^{-3}$) with an impurity dopant. A lower electrode 58 may then be deposited below the substrate 50 (or below the gain medium 18), and an upper electrode 60 may be deposited above the gain medium. The upper electrode 60 may be a planar transparent electrode (e.g. indium tin oxide) overlying the gain region 18; or the upper electrode may overlie the patterned insulating layer 54 in the analysis region 20 as shown in FIG. 3b. (The upper electrode may be considered to be within the analysis region 20, and to form a part of the analysis region in the example of FIG. 3b). The upper electrode 60 preferably extends downward through the container or flow channel to contact an upper surface of the gain medium 18 (i.e. one side of the p-n junction). An electrical current may then be provided to flow between the lower and upper electrodes (58 and 60, respectively) to the p-n junction in the gain medium to generate optical gain in an activated portion 52 of the gain medium to promote lasing action in the laser cavity. Ion implantation or selective etching may be used to remove a portion of the gain layer beyond the activated portion for further defining the activated portion of the gain medium 18.

In the examples of FIGS. 3a and 3b, the laser beam 22 is generated within the laser 12 by the gain medium 18 acting in combination with one or more biological cells 100 present within the analysis region 20. The gain medium 18 may be activated by the pump means to provide a low gain for the cavity so that in the absence of any cell within the analysis region, the laser 12 is below a threshold for lasing and no laser beam 22 is generated. In this case, only a weak, featureless spontaneous emission spot from the activated portion 52 may be measured by the analysis means 24.

The introduction of a biological cell into the analysis region may then result in the redirection of photons and improved waveguiding thereof so that lasing action occurs in at least a portion of the cell and a laser beam 22 is generated. Alternately, the gain medium 18 may be activated to provide a high gain for the cavity so that a laser beam 22 is generated with or without a biological cell 100 present in the cavity, with the cell acting to alter or modify an optical characteristic of the laser beam such as an emission spectrum, a transverse mode profile, an optical intensity, a nonlinear optical signal (e.g. generated by polar molecules within the cell), a lasing threshold characteristic (e.g. the introduction of a cell into the analysis region may alter a threshold for lasing of the laser 12, producing lasing within a below-threshold laser or suppressing lasing within an above-threshold laser), or a combination thereof. In any case, one or more optical characteristics of the laser beam 22 may be determined at least in part by portions of the cell, thereby impressing (i.e. encoding) information about the cell upon the laser beam. Furthermore, the laser 12 may be operated below threshold with or without a cell present in the analysis region; and the introduction of a cell to the analysis region may act to locally alter a phase of amplified spontaneous emission from the laser, thereby providing an analysis image of the cell or its components.

Figure 4A:
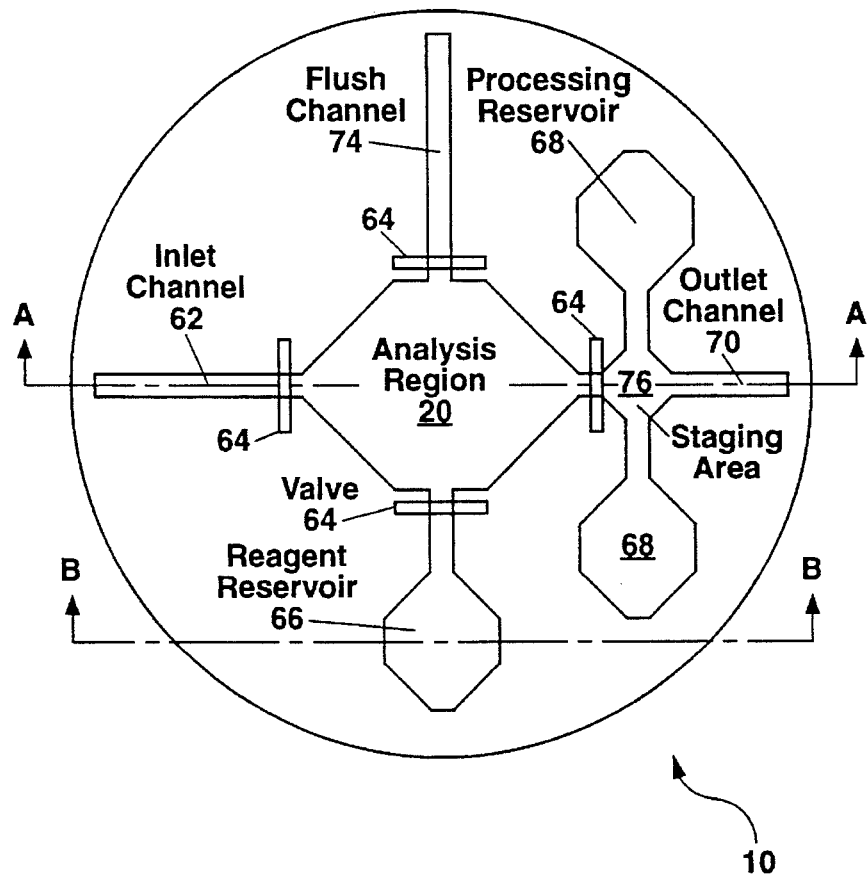
FIG. 4a shows a third example of a laser biological cell analyzer according to the present invention including means for processing biological cells after analysis thereof.

FIG. 4 shows a third example of the present invention of a laser apparatus 10 for microscopic and spectroscopic analysis and processing of biological cells. In FIG. 4a, the apparatus 10 is formed as a compact device, preferably having an inlet channel 62 for admitting one or more biological cells 100 suspended in a carrier fluid 102 into the device. The inlet channel 62 may be connected to means for supplying the biological cells such as described heretofore. The cells upon entering the apparatus 10 may be transported through the inlet channel 62 to an analysis region 20 as shown in FIG. 4a. The analysis region may be capable of being isolated from the inlet channel 62 by a valve 64. The valve 64 may be, for example, a gate valve operated electrically (e.g. by an electrostatic motion of a hinged valve, or by a micromotor that is connected by a micromechanical gear train to move a valve gate between an open and a closed position), hydraulically (e.g. by a piston or gate moveable within the channel between an open and a closed position), or pneumatically (in a manner similar to a hydraulically operated valve 64), or optically (e.g. by the use of "photon tweezers" to move a particle or block of material between an open and a closed position in the channel) for opening and closing the valve 64 to allow the passage of one or more cells 100 therethrough. The valve 64 may be formed as a micromechanical device in a micromachineable substrate 50 (e.g. a silicon substrate) as known to the art of micromechanics.

The cells 100 to be analyzed may be transported into the analysis region 20 by the use of a flow stream in the inlet channel 62 for analysis thereof. The analysis region 20 may be connected by additional flow channels (with additional valves 64 which may be opened and closed for transport of the cells into and out from the analysis region 20) to additional regions of the apparatus including one or more reagent reservoirs 66, and one or more processing reservoirs 68 as shown in FIG. 4a. The reagent reservoirs 66 may be provided with agents such as cell stimulants, drugs, or reagents (e.g. monoclonal antibodies, or nucleic acids) that may act to modify cell properties; and these agents may be introduced into and/or flushed from the analysis region by flow channels for analyzing a response of the cell to these agents. A flush channel 74 may be provided for introducing fluids into and/or out from the analysis region 20 for cleansing thereof.

Figure 4B:
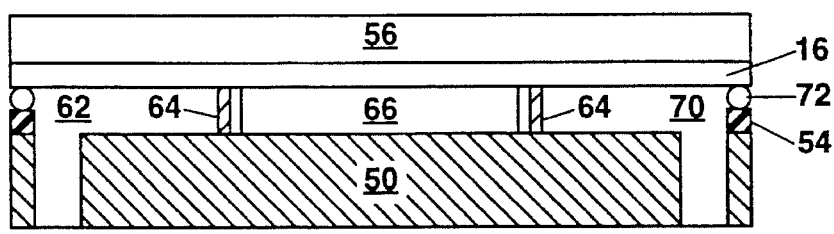
FIG. 4b shows a schematic cross-section view of the apparatus of FIG. 4a along the line 1—1.
Figure 4C:
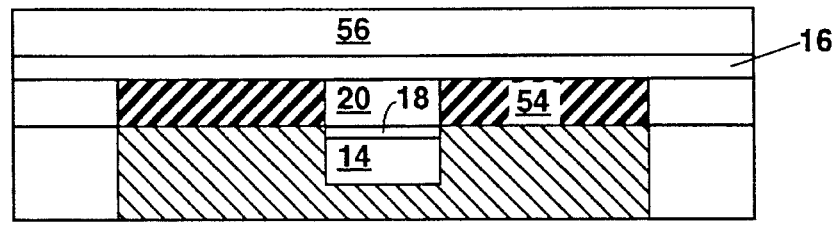
FIG. 4c shows a schematic cross-section view of the apparatus of FIG. 4a along the line 2—2.

The analysis region 20 is located within the cavity of a laser 12 formed as described heretofore. In this example of the present invention, it may be preferable to fabricate the apparatus 10 on a micromachineable substrate 50 such as silicon or the like that allows the formation of the flow channels and valves by micromechanical processing as known to the art. In this case, the laser 12 may comprise a lower mirror 14 and a gain medium 18 that may be attached to the substrate 50 in an etched well thereof as shown in view 2 in FIG. 4c. The upper mirror 16 of the laser 12 may be formed on a transparent substrate 56 as described heretofore, with the transparent substrate being in contact with a patterned insulating layer 54 formed above the silicon substrate 50 as shown in FIGS. 4b and 4c. A liquid-tight seal 72 such as an o-ring or the like; or an adhesive may be provided between the patterned insulating layer 54 and the upper mirror 16 as shown in view 1 in FIG. 4b; or alternately, the surfaces of the layer 54 and the mirror 16 may be flat enough so that a liquid-tight seal may be formed when the insulating layer and upper mirror are brought into contact and held together by a clamp.

After analysis of the biological cells 100, the cells may be transported to a processing region comprising, for example, a pair of processing reservoirs 68 with a staging area 76 therebetween. The cells may be selectively manipulated, sorted, or eradicated in the staging area 76 of the processing region according to the information recovered from the cells by the analysis means 24. The apparatus 10 may further comprise one or more outlet channels 70 for clearing cells from the apparatus of for aiding in transporting the cells to and from the analysis and processing regions.

The compactness of the apparatus of FIG. 4 (which may have lateral dimensions of a few inches or less) is advantageous in allowing the apparatus 10 to be positioned under a microscope for visual observation and/or for optically pumping the apparatus with a pump laser 26. The third example of the invention in FIG. 4 may have applications as a microlaboratory for conducting experiments in real time on biological cells. In addition, a plurality of parallel or interconnected laser biological cell analyzers 10 may be formed according to the present invention on a single substrate 50.

FIGS. 5–10 show calculations and measurements made according to the present invention, including measurements of normal and abnormal human red blood cells and normal human white blood cells. These calculations and measurements demonstrate the ability of the apparatus 10 to distinguish different sizes, types, and variants of biological cells and to selectively analyze constituents thereof.

FIG. 5 shows calculated wavelengths of transverse lasing modes (i.e. eigenmodes) of the laser 12 for a cell 100 having cylindrical symmetry (viewed along the direction of the laser beam 22) with a diameter of 7.5 µm and a refractive index of 1.4. (The wavelength shift in FIG. 5 is measured as a deviation from an unperturbed cavity wavelength of about 850 nm in the absence of any cell in the laser cavity.) In FIG. 5, the absolute wavelengths of the eigenmodes are given by:

$$\lambda_{lmn} = \frac{2\pi n_1}{\sqrt{\left(\frac{2\pi l - \phi}{2L}\right)^2 + \left(\frac{2x_{mn}}{d}\right)^2}}$$

where $n_1$ is the refractive index of the cell (in a carrier fluid of refractive index $n_2$), L is an integer corresponding to a longitudinal eigenmode, $\Phi$ is a sum of the phases of the cavity mirrors located at positions -L/2 and L/2 along the cavity axis (denoted herein as the z axis), $x_{mn}$ is an nth zero of the mth Bessel function, and d is the cell diameter. Under normal conditions, the longitudinal modes in a vertical-cavity surface-emitting semiconductor laser 12 may be spaced more widely than the gain spectrum so that only a single longitudinal mode lases in the unperturbed laser cavity. The transverse modes in the cavity, however, have a smaller wavelength separation so that a large number of transverse modes may support lasing. Furthermore, two polarizations corresponding to a transverse electric (TE) state and a transverse magnetic (TM) state may be associated with each transverse lasing mode.

The emission spectrum of the transverse lasing modes may be strongly influenced by the optical and structural properties of a cell 100 placed within the cavity of the laser 12. A wavelength separation of the transverse modes from a given longitudinal wavelength (taken as zero wavelength shift in FIG. 5) is given by:

$$\Delta\lambda_{mn} = \frac{-\lambda^2 x_{mn}^2}{2\pi^2 n_1^2 d^2}$$

In the above equation, the wavelength separation, $\Delta\lambda$, of the transverse modes is dependent on the cell diameter, d, and also on the cell shape due to $x_{mn}$ parameter (as shown in FIG. 5). The above equation for $\Delta\lambda$ is expected to be accurate for low-index transverse lasing modes (i.e. low values of m and n) for which the electric field of the laser beam may be localized within the cell. For higher-index transverse lasing modes (i.e. high values of m and n), the electric field may extend beyond the cell boundaries; and the above model may be less accurate, with the wavelength separation, $\Delta\lambda$ being smaller than would be calculated from the above equation. Thus, the above equation for $\Delta\lambda$ shows that the lasing emission spectrum of the laser beam 22 may be used to recover information about the size and shape of the cell or its component.

In FIG. 5, the inset photographs show experimentally measured profiles for the six lowest-order transverse lasing modes in the apparatus 10 with normal human red blood cells (of different sizes to stimulate lasing in the different transverse modes) in the laser cavity. Each image in FIG. 5 corresponds to a single transverse eigenmode of the lair cavity as recorded with either a cw or nanosecond pulsed pump laser 26. With these pump lasers, the gain bandwidth of the gain medium 18 is small, and generally only one transverse lasing mode is observed.

In FIG. 5, the transverse mode profile images show that the number of nodes and the lateral dimensions or spatial extent of a mode increases as the mode indices (m and n) increase. (In FIG. 5, the mode indices, m and n, denote the number of angular and radial nodes (dark areas), respectively.) In the samples of normal human red blood cells studied to date, the frequency of occurrence of a given mode depends on the distribution of cell sizes and shapes in a blood sample. The most frequently occurring transverse mode is the $TEM_{10}$ mode. This double-lobed mode is characteristic of about 50% of normal human red blood cells in a plasma carrier fluid in the physiologic state. Another common transverse lasing mode (not shown in FIG. 5) occurring in about 10% of normal human red blood cells is observed as a ring-shaped mode profile, and is designated $TEM_{10}*$ (where the star superscript denotes a linear combination of horizontal and vertical versions of the $TEM_{10}$ mode). Both the $TEM_{10}$ and $TEM_{10}*$ modes are consistent with the toroidal or biconcave shape of normal human red blood cells as shown in FIG. 2.

The fundamental $TEM_{00}$ mode in FIG. 5 occurs in only about 15% of normal human red blood cells, and is associated with cells that have lost some of their biconcavity; or with smaller blood cells. The higher-order transverse lasing modes $TEM_{20}$ (with a cloverleaf shape), $TEM_{30}$ (with a hexagonal shape), $TEM_{01}$ (with a dot and surrounding ring shape), and $TEM_{02}$ (with a split dot and ring shape) are observed much less frequently, each accounting for only a few percent of the total distribution of normal human red blood cells studied to date. These higher-order transverse lasing modes occur in the largest red blood cells for which the higher-order modes are stable.

Figure 7:
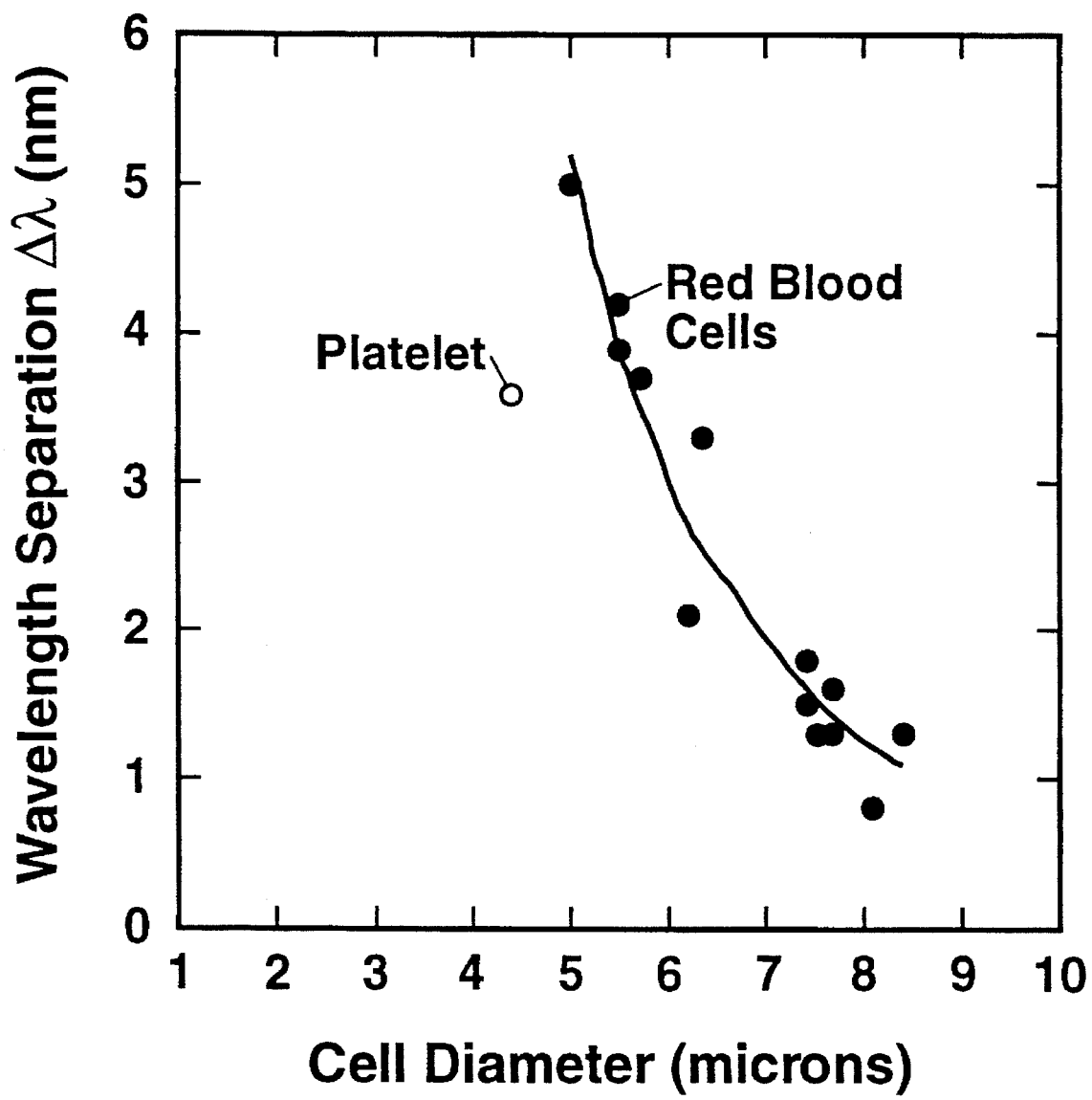
FIG. 7 shows the correlation of the diameter of normal human red blood cells and the wavelength separation, $\Delta\lambda$, between the $TEM_{00}$ and $TEM_{10}$ modes of the laser beam generated by the apparatus of the present invention.

A femtosecond pump laser 26 may also be used according to the present invention. In this case, the gain in the laser 12 may be much larger and the gain bandwidth wider so that a plurality of transverse lasing modes may lase simultaneously in the laser beam 22. The observed distribution of intensities of each of the lasing modes will depend on the relative gain and loss for each mode, and may be measured with the spectrometer 38 in the analysis means 24. The relative optical loss in the laser cavity of a particular transverse lasing mode will depend on the cell size, shape, and structure, the ability of the cell to redirect light rays, and any localized absorption or scattering losses in the cell. In general, the wavelength separation of the transverse lasing modes will decrease with increasing cell diameter, d, according to the above equation for $\Delta\lambda$, as shown in FIG. 7.

Figure 6A:
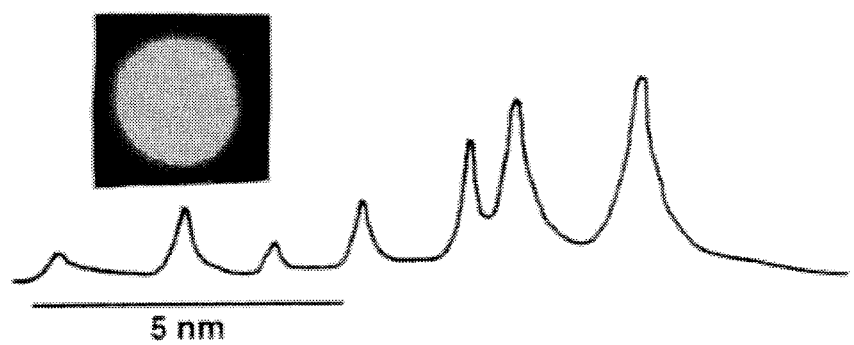
FIGS. 6a, 6b, and 6c show multimode emission spectra and transverse mode profiles generated by the apparatus of the present invention for different sizes of normal human red blood cells with the laser operated at a high gain.
Figure 6B:
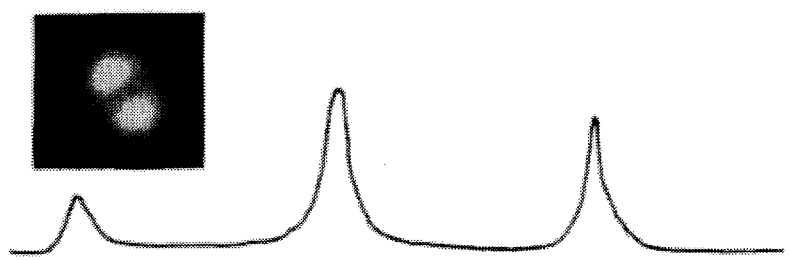
Figure 6C:
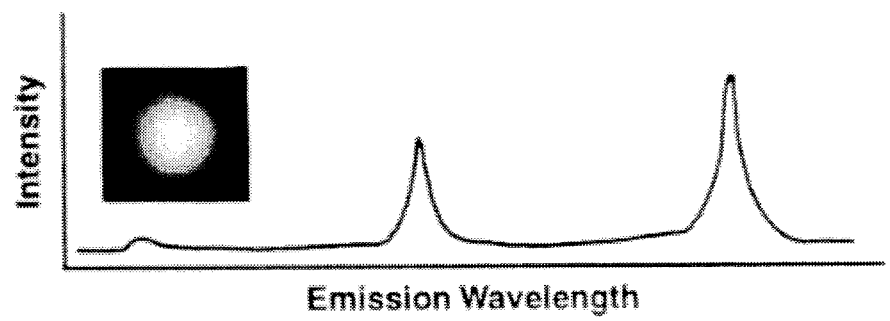

FIG. 6 shows the emission spectra (recorded with the spectrometer 38) and lasing mode images (recorded with a CCD camera 36) for three normal human red blood cells of different sizes as measured with the apparatus 10 with a femtosecond pump laser 26. The cell diameters are about 7.5 μm, 5.7 μm, and 5.0 μm, for FIGS. 6a, 6b, and 6c, respectively. In each case in FIG. 6, the spectra and images comprise a plurality of different transverse modes lasing simultaneously. The emission spectra in FIG. 6 have been recorded on a logarithmic intensity scale (i.e. the intensity scale spans three orders of magnitude from the highest intensity peaks in FIG. 6 to the lowest background signal between the peaks) to enhance observation and measurement of the weaker modes. No absolute wavelength scale is provided in FIG. 6 (although a relative wavelength shift-scale is provided) since the different cells were examined at different positions in the analysis region 20, resulting in slightly different cavity lengths, L, between the reflecting mirrors and therefore different absolute wavelengths, $\lambda_{lmn}$, for the longitudinal cavity mode. Only the relative positions of the peaks in FIG. 6 appear to be correlated with properties of the cells. The spectra in FIG. 6 are recorded with the longest wavelength to the right, and a 5 nm-wide wavelength marker is provided for calibrating the wavelength separation between the transverse lasing modes in any of the emission spectra.

In FIG. 6, the positions of the lasing peaks in the emission spectra are substantially insensitive to the intensity of the pump laser 26 over a wide range, indicating that the cell geometry is primarily responsible for the spectral distribution of the lasing modes in the laser 12. In FIG. 6c, the emission spectrum of a small 5.0-μm-diameter cell shows a dominant peak corresponding to the $TEM_{00}$ lasing mode, and a second weaker peak corresponding to the $TEM_{10}$ mode. The wavelength separation of the two peaks in the emission spectrum of FIG. 6c is relatively wide (about 5.5 nm) due to the small size of this particular red blood cell. The inset image in FIG. 6c appears as a circular (i.e. Gaussian) disk, consistent with the mode distribution of the emission spectrum (i.e. a dominant $TEM_{10}$ lasing mode). This may indicate that the smaller blood cell in FIG. 6c has less biconcavity, therefore favoring lasing in the fundamental $TEM_{00}$ mode.

FIG. 6b shows similar data for a 5.7 μm-diameter normal human red blood cell. For this cell, the $TEM_{10}$ mode (the central peak in the spectrum of FIG. 6b) is dominant in the emission spectrum, with a less intense $TEM_{00}$ lasing mode, and a very weak $TEM_{20}$ lasing mode. The wavelength separation between the $TEM_{00}$ and $TEM_{10}$ lasing modes in FIG. 6b is reduced to about 4.6 nm, consistent with the larger size of this cell. The dominant $TEM_{10}$ mode is also evident in the inset image in FIG. 6b, indicating that this cell has more biconcavity than the cell of FIG. 6c.

FIG. 6a shows yet more data for another red blood cell having a larger diameter of 7.5 μm. The emission spectrum for this cell is more complicated, showing seven transverse lasing modes. The dominant lasing mode as determined by lowering the pump power from the pump laser 26 is the $TEM_{10}$ mode. In FIG. 6a, the higher-order transverse modes have peak emission intensities that for the most part decrease with increasing mode order (and to shorter lasing wavelengths). The wavelength separation between these transverse modes is much smaller (only about 1–2 nm) due to the larger size of this cell. The wavelength separation between the lowest-order modes in FIG. 6a is in general agreement with the calculated mode positions in FIG. 5. However, the wavelength separation between the three highest-order modes (i.e. the three leftmost peaks in the emission spectrum of FIG. 6a) is much less than predicted, indicating that some of the electric field intensity for these modes may be outside the cell boundary.

In FIG. 7, the wavelength separation between the $TEM_{00}$ and $TEM_{10}$ lasing modes is plotted against the cell diameter as measured visually through a microscope for a number of normal human red blood cells. From these measurements, it may be seen that the wavelength separation increases from about 1 nm for the largest cells to about 5 nm for the smallest cells. (Normal red blood cells have diameters that are generally in the range of about 6.5 to 8.5 μm; and the small-diameter red blood cells in FIG. 7 were obtained from a sickled blood smear.) Thus, the apparatus 10 of the present invention may be used to analyze biological cells according to size as shown in FIG. 7.

Figure 8A:
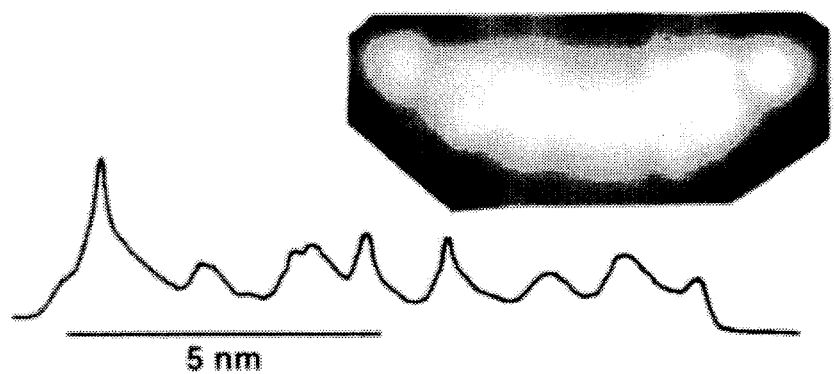
FIGS. 8a, 8b, and 8c show emission spectra and transverse mode profiles generated by the apparatus of the present invention for different sizes of abnormal human red blood cells (i.e. sickle cells) with the laser operated at a high gain.
Figure 8B:
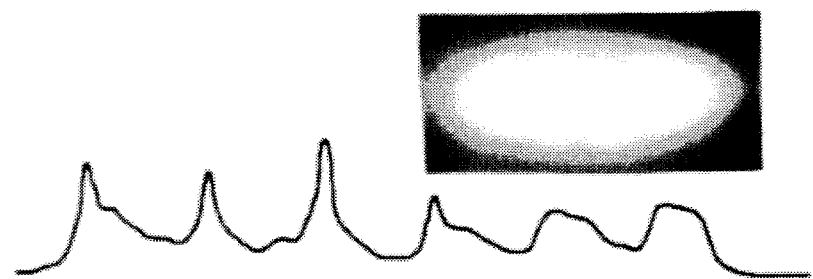
Figure 8C:
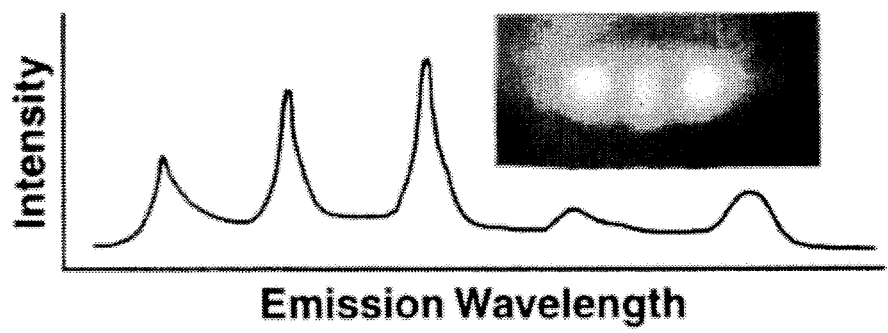

FIG. 8 shows measurements with the apparatus 10 for sickled red blood cells, one of the best understood of molecular diseases. In these abnormal cells, the hemoglobin molecule (HbS) has one amino acid substitution in the β globulin chain which causes the HbS protein to partially crystallize within the cell. With both solid and liquid phases present, the cell acquires the characteristic shape of a sickle, having a long, thin shape that is distinctly different from normal red blood cells. Whole blood from a patient with sickle cell anemia (HbSS) was drawn and diluted in an isotonic media (i.e. carrier fluid) and tested in the apparatus 10 of the present invention under high gain conditions in a manner to that described heretofore for FIG. 6. The sickle shape of these abnormal red blood cells results in transverse lasing modes that are characterized by nodes along the long and short axes of the sickle cell as shown in FIG. 8 for three different sickle cells of lengths from about 8.2 μm to about 11.6 μm. In FIG. 8, each of the images recorded with the analysis means 24 for the laser 12 shows the linear geometry of the sickle cells, and a number of nodes along one or more axes of the sickle cells. The number of nodes in the laser beam 22 increases from two for an 8.2 μm-long cell in FIG. 8c to three for a 9.0 μm-long cell in FIG. 8b, and to seven (six nodes in the vertical direction and one node in the horizontal direction) for the 11.6 μm-long cell in FIG. 8a. The image of FIG. 8c indicates that the lowest-order transverse lasing modes $TEM_{11}$ and $TEM_{21}$ expected for a cell of this shape are not present to any significant extent. This is confirmed from the emission spectra in FIG. 8 which show very broad and weak peaks at the longest wavelengths (to the right in FIG. 8c) indicating amplified spontaneous emission but no lasing at the wavelengths of these lowest-order modes. Instead, the two nodes (i.e. the two dark vertical lines) in the image of FIG. 8c and the location of the strong emission peak in the spectrum both indicate that the dominant lasing mode for this small-size sickle cell is the $TEM_{31}$ mode. (Calculated emission wavelengths and transverse mode profiles for sickle cells are disclosed in the aforementioned article by P. L. Gourley et al.)

In FIG. 8b, the lasing emission spectrum shows three broad, weak peaks at long wavelengths and three stronger and narrower peaks at shorter wavelengths. The weak peaks correspond to the $TEM_{11}$, $TEM_{21}$, and $TEM_{31}$ modes (to shorter wavelengths, respectively) which are either not lasing, or only very weakly lasing. The dominant lasing peak in the spectrum of FIG. 8b is the $TEM_{41}$ mode (the fourth peak from the right) which corresponds to a transverse mode profile having three vertical nodes as in the image of FIG. 8b.

In FIG. 8a, many closely spaced peaks are present in the lasing emission spectrum due to the large size of this sickle cell (11.6 μm long) thereby complicating the interpretation of the emission spectrum. In this spectrum, the peaks are not as uniformly spaced as in FIGS. 8b and 8c, and the distribution of the lasing modes is less well defined. One peak on the extreme left side of the spectrum is dominant, corresponding to the $TEM_{71}$ lasing mode. This transverse mode has six vertical nodes consistent with the image in FIG. 8a. Two weaker lasing modes are also present in the spectrum of FIG. 8a, with the remaining broad, weak peaks being the result of amplified spontaneous emission, but not lasing.

The images and spectra for sickle cells as measured by the apparatus 10 and shown in FIG. 8 are markedly different from the measurements for normal human red blood cells as shown in FIG. 6, thus showing the utility of the apparatus of the present invention for distinguishing between cell types or variants (i.e. between normal and abnormal or diseased cells).

White blood cells are much more complex than red blood cells. White blood cells are larger, vary in shape, and contain a nucleus and other smaller organelles within the cytoplasm. In addition there are several different types of white blood cells classed as polymorphonuclear leukocytes (including polymorphonuclear neutrophils, polymorphonuclear eosinophils, and polymorphonuclear basophils), lymphocytes, and monocytes. This complexity leads to lasing images and spectrum as measured by the apparatus 10 that are rich in structure. Whereas, an entire red blood cell may support lasing, a white blood cell generally only supports lasing in the condensed matter of the nucleus or in the peripheral region outside the nucleus bounded by the cell membrane. In addition, the nucleolus and some larger complexes outside the nucleus may also support lasing. Lasing modes in two common types of white blood cells are described hereinafter.

A first type of white blood cell, polymorphonuclear leukocytes (about 15 μm diameter) comprise a condensed nucleus inside the cell segmented into several irregular lobes (of about 3–5 μm size); small complexes (with dimensions of about 10–100 nm) including mitochondria, golgi bodies, and endoplasmic reticula; and granules (with dimensions of about 200–500 μm) inside a membrane with tiny finger-like projections therefrom (about 100–200 nm long). Optically, all of these structures are substantially transparent to infrared light. The condensed nucleus has convex surfaces and a higher refractive index than surrounding cytoplasm. Some scattering loss may occur from the granules and membrane fingers, but this is not sufficient to prevent the generation of lasing when the cells are in the analysis region 20 of the laser 12 in the apparatus 10.

With the apparatus of the present invention, images of polymorphonuclear neutrophils (a particular type of a polymorphonuclear leukocyte) from whole blood may be obtained with the laser 12 either operated below or above a threshold for lasing. Below the lasing threshold, the periphery of the cells in an analysis image appears bright (as a sheath that is a few microns thick) compared to the cytoplasm and the external plasma. The bright sheath is likely due to light scattering from the fingered membrane surface of the cell and/or a cytoskeletal network forming the plasma membrane. Within the white blood cell are light and dark regions with low contrast so that the nucleus is not visibly apparent.

As the power in the pump laser beam 28 is increased, amplified spontaneous emission in the laser 12 begins to build up, increasing the image contrast of the white blood cell and making the nucleus in the cell appear brighter than the light scattered at the membrane. As the power in the pump laser beam 28 is further increased, the cell nucleus begins to support lasing, with the lasing emission at the positions of the cell nucleus being many orders of magnitude brighter than the surrounding spontaneously emitted and scattered light from other parts of the cell. Lasing in multiple transverse modes is typical for white blood cells, even under low gain conditions where the gain bandwidth of the laser 12 is reduced.

Figure 9:
FIG. 9 shows a confocal laser scanning reflected light image of a normal human lymphocyte cell.

With the apparatus 10, a second type of white blood cells, lymphocytes, may also be analyzed with images and spectra generated and recorded to quantify protein/nucleic acid concentrations, and states of activation and proliferation. Lymphocytes are about 10 μm in diameter with a large nucleus that nearly fills the entire cell. FIG. 9 shows a laser scanning confocal micrograph image of a lymphocyte dried in air and placed on a dielectric mirror. In FIG. 9, the large nucleus of the lymphocyte is visible as an oval shape substantially filling the image shown.

Figures 10A, 10B, 10C:
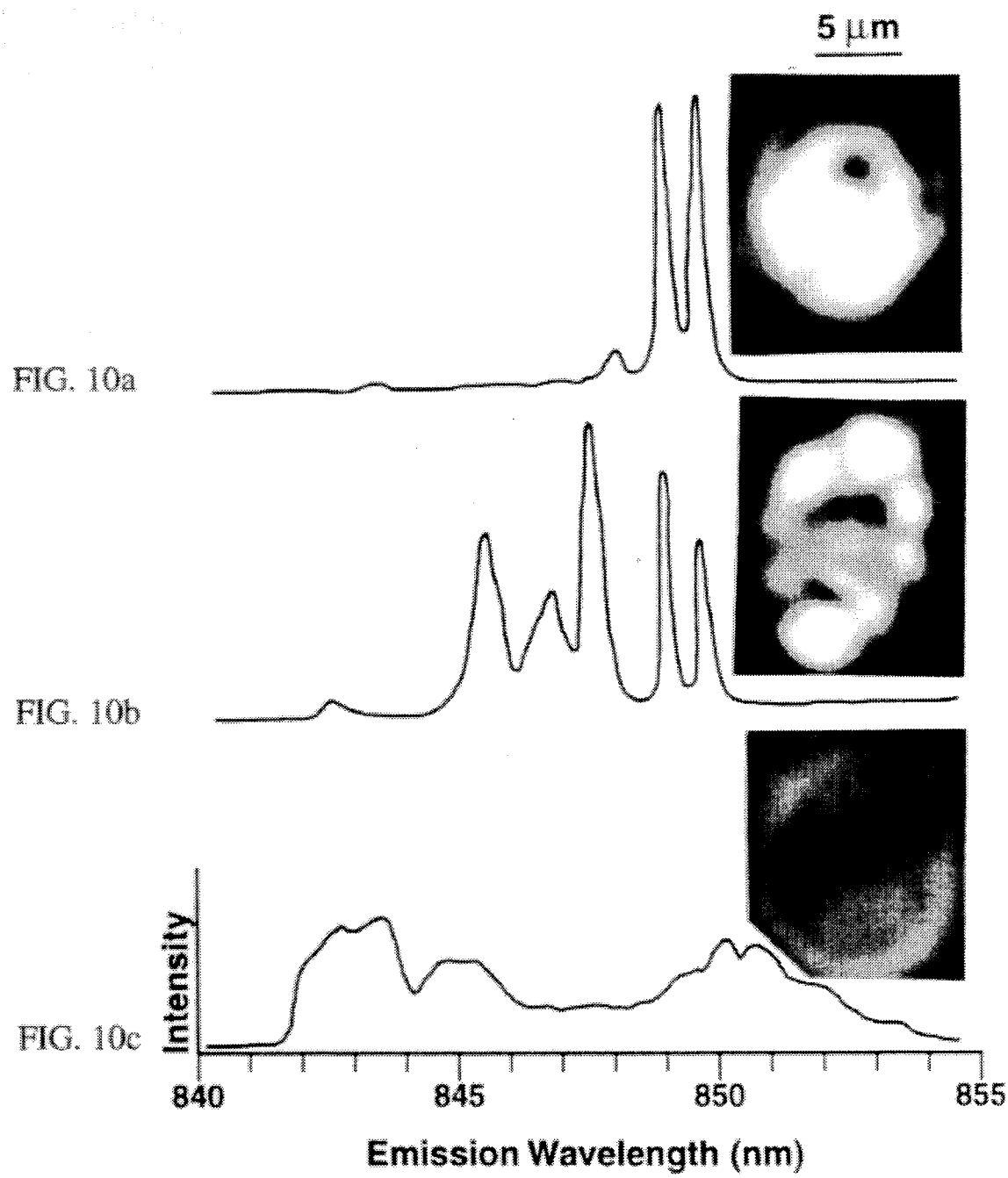
FIGS. 10a, 10b, and 10c show emission spectra and transverse mode profiles generated by the apparatus of the present invention for the normal human lymphocyte cell of FIG. 9 with the laser operated at a low gain.

FIG. 10 shows measurements for this same lymphocyte made with the apparatus of the present invention after placing the lymphocyte within the analysis region 20 in the laser 12. In FIG. 10c, with the laser 12 operating below the lasing threshold, an outer membrane of the lymphocyte is highlighted and the emission spectrum shows two broad peaks centered at wavelengths near 843 and 851 nm, respectively.

FIGS. 10a and 10b show the laser 12 operated above threshold, with the focused pump laser beam being concentric and eccentric with the lymphocyte, respectively. In FIG. 10a, the large nucleus supports lasing in a plurality of transverse modes with peaks in the emission spectrum appearing at wavelengths near 848, 849, and 850 nm. All the transverse lasing modes in FIG. 10a are confined to the nucleus, and reveal subtle variations not apparent in the confocal image of FIG. 9.

The wavelength separation between the transverse modes in the emission spectrum is small (about 1 nm) due to the large size of the lymphocyte. Thus, the apparatus 10 is capable of measuring cell sizes as discussed heretofore with reference to FIG. 7. This ability to measure cell sizes may be advantageous for analyzing cancerous cells that exhibit changes in sizes as compared to normal cells.

In FIG. 10b, eccentric optical pumping of the gain medium 18 results in lasing in a number of filaments substantially around the periphery of the lymphocyte, with the center of the nucleus being relatively dark. Under these conditions, the lasing modes are localized closer to the outer surface of the lymphocyte, and are more sensitive to surface conditions of the cell and its outer membrane. The emission spectrum of FIG. 10b is also distinctly different from that of FIG. 10a, showing a different distribution and number of peaks, with new peaks occurring in the wavelength range between 845 and 848 nm. Thus FIG. 10 shows that the apparatus 10 may be used to analyze the nucleus and cell membrane in a lymphocyte and measure microscopic and spectroscopic differences thereof.

In addition to the measurements described heretofore, the apparatus 10 of the present invention may also be used to analyze other types of cells including blood platelets. Blood platelets may be in the shape of small disks with a diameter of about 4 µm or less. The lasing mode for a platelet within the analysis region 20 of the laser 12 generally appears circular (i.e. Gaussian), indicating lasing in a $TEM_{00}$ mode; and the emission spectrum shows a single sharp peak corresponding to lasing in only one transverse mode.

The matter set forth in the foregoing description and accompanying drawings is offered by way of illustration only and not as a limitation. Other applications and variations of the laser apparatus and method of the present invention for microscopic and spectroscopic analysis and processing biological cells will become evident to those skilled in the art from practice of the invention. Examples of such applications may include probing human or animal cells for characterizing immune systems (e.g. for analyzing surface properties of leukocytes); characterizing human or animal genetic disorders (e.g. for analyzing a crystallization of hemoglobin in sickled red blood cells); analyzing and processing cell types (e.g. sorting XX and XY sperm for sex selection or in-vitro fertilization); and analyzing cancerous cells. The actual scope of the invention is intended to be defined in the following claims when viewed in their proper perspective based on the prior art.

What is claimed is:

1. Apparatus for analyzing biological cells comprising:
   (a) a laser having a resonant optical cavity formed by at least two reflecting mirrors, a gain medium within the resonant optical cavity, and pump means for activating the gain medium; and
   (b) an analysis region located within the resonant optical cavity for containing at least one biological cell to be analyzed, the analysis region being disposed along a central portion of the cavity wherein a laser beam is generated by the laser at least partially in response to one of the biological cells present within the analysis region, the lasers beam having information about the biological cell encoded thereupon.

2. The apparatus of claim 1 further including analysis means for receiving a portion of the laser beam and recovering the information about the biological cells.

3. The apparatus of claim 2 in which the information is in the form of an optical characteristic of the laser beam selected from the group consisting of an emission spectrum, a transverse mode profile, an optical intensity, a nonlinear optical signal, a lasing threshold characteristic, or a combination thereof.

4. The apparatus of claim 2 further including processing means for processing of the biological cells.

5. The apparatus of claim 4 in which the processing means includes at least one manipulation laser.

6. The apparatus of claim 1 in which the analysis region is located within a flow cell.

7. The apparatus of claim 6 further including means for supplying the biological cells to the flow cell, and means for accumulating the biological cells after passing through the flow cell.

8. The apparatus of claim 1 in which the gain medium comprises at least in part a fluorescent stain.

9. The apparatus of claim 1 in which the laser beam has an emission wavelength within the wavelength range of about 600 to about 1500 nanometers.

10. The apparatus of claim 1 in which the means for activating the gain medium is a pump laser having a pump beam directed into the gain medium to provide an activated portion thereof.

11. The apparatus of claim 10 further including steering means for steering the pump beam to activate a particular part of the gain medium.

12. The apparatus of claim 1 in which the laser is a semiconductor laser.

13. The apparatus of claim 12 in which the semiconductor laser is a vertical-cavity surface-emitting laser.

14. The apparatus of claim 13 in which one of the reflecting mirrors is a distributed Bragg reflector mirror on a semiconductor substrate, and another reflecting mirror is located on a transparent substrate above the semiconductor substrate.

15. The apparatus of claim 13 in which the pump means for activating the gain medium is a pump laser having a pump beam directed into the gain medium to provide an activated portion thereof.

16. The apparatus of claim 15 further including steering means for steering the pump beam to activate a particular part of the gain medium.

17. The apparatus of claim 13 in which the gain medium includes a semiconductor p-n junction, and the pump means for activating the gain medium is an electrical current.

18. Apparatus for analyzing biological cells comprising:
   (a) a first substrate having a lower reflecting mirror thereon, and a gain medium above the lower reflecting mirror;
   (b) a second substrate having an upper reflecting mirror formed on a lower surface thereof, the upper and lower reflecting mirrors forming a resonant optical cavity;
   (c) an analysis region within the resonant optical cavity for containing at least one biological cell to be analyzed, the analysis region being disposed along a central portion of the cavity; and
   (d) pump means for activating the gain medium to generate in combination with one of the cells present within the central portion of the cavity a laser beam having information about the biological cell encoded thereupon.

19. The apparatus of claim 18 in which the lower reflecting mirror is a distributed Bragg reflector mirror.

20. The apparatus of claim 18 in which the pump means for activating the gain medium is a pump laser having a pump beam directed into the gain medium to provide an activated portion thereof.

21. The apparatus of claim 20 further including steering means for steering the pump beam to activate a particular part of the gain medium.

22. The apparatus of claim 18 in which the gain medium includes a semiconductor p-n junction, and the pump means for activating the gain medium is an electrical current.

23. The apparatus of claim 18 further including analysis means for receiving a portion of the laser beam and recovering the information about the biological cells.

24. The apparatus of claim 23 in which the information is in the form of an optical characteristic of the laser beam selected from the group consisting of an emission spectrum, a transverse mode profile, an optical intensity, a nonlinear optical signal, a lasing threshold characteristic, or a combination thereof.

25. The apparatus of claim 23 further including processing means for processing the biological cells.

26. The apparatus of claim 25 in which the processing means includes at least one manipulation laser.

27. The apparatus of claim 18 in which the analysis region is located within a flow cell.

28. The apparatus of claim 27 further including means for supplying the biological cells to the flow cell, and means for accumulating the biological cells after passing through the flow cell.

29. The apparatus of claim 18 in which the gain medium comprises at least in part a fluorescent stain.

30. The apparatus of claim 18 in which the laser beam has an emission wavelength within the wavelength range of about 600 to about 1500 nanometers.

31. A method for analyzing biological cells comprising the steps of:
   (a) locating at least one cell to be analyzed within an analysis region within a resonant optical cavity of a laser;
   (b) activating a gain medium within the laser by a pump means and generating a laser beam within the cavity of the laser; and
   (c) encoding the laser beam with information about at least one of the biological cells present in the analysis region.

32. The method of claim 31 further including the step of recovering the information about the cell by measuring at least one optical characteristic of the laser beam by analysis means.

33. The method of claim 32 in which the optical characteristic is selected from the group consisting of an emission spectrum, a transverse mode profile, an optical intensity, a nonlinear optical signal, a lasing threshold characteristic, or a combination thereof.

34. The method of claim 32 in which the pump means is a pump laser for optically activating the gain medium.

35. The method of claim 34 further including the step of steering a pump beam from the pump laser to activate a particular part of the gain medium for analyzing at least one cell in superposition therewith.

36. The method of claim 32 further including the step of processing a plurality of biological cells after analyzing the cells and recovering information thereabout.

37. The method of claim 36 in which the step of processing the cells includes at least one process selected from the group consisting of sorting, manipulating, or eradicating cells.

38. The method of claim 31 further including the steps of supplying a biological cells to the analysis region located within a flow cell, and accumulating the biological cells after passing through the flow cell.

39. The method of claim 38 further including the step of activating at least one valve for supplying the biological cells to the analysis region.

40. The method of claim 31 further including the step of staining the cells with a fluorescent stain.

41. The method of claim 40 wherein the fluorescent stain comprises at least a part of the gain medium.

42. Apparatus for analyzing biological cells comprising:
   (a) a first laser having a resonant optical cavity including a gain medium and an analysis region for containing at least one biological cell to be analyzed; and
   (b) a second laser for activating the gain medium to generate a laser beam within the resonant optical cavity of the first laser, with the laser beam having information about the biological cell encoded thereupon.

43. The apparatus of claim 42 in which the first laser is a vertical-cavity surface-emitting laser.

* * * * *